United States Patent
Czibula et al.

(10) Patent No.: US 7,625,935 B2
(45) Date of Patent: Dec. 1, 2009

(54) HIGH PURITY BUTOCONAZOLE NITRATE WITH SPECIFIED PARTICLE SIZE AND A PROCESS FOR THE PREPARATION THEREOF

(75) Inventors: Laszlo Czibula, Budapest (HU); Laszlo Dobay, Budapest (HU); Eva Werkne Papp, Budapest (HU); Judit Nagyne Bagdy, Budapest (HU); Ferenc Sebok, Mezokovacshaza (HU)

(73) Assignee: Richter Gedeon Vegyeszeti Gyar Rt., Budapest (HU)

( * ) Notice: Subject to any disclaimer, the term of this patent is extended or adjusted under 35 U.S.C. 154(b) by 553 days.

(21) Appl. No.: 10/584,662

(22) PCT Filed: Jan. 25, 2005

(86) PCT No.: PCT/HU2005/000002
§ 371 (c)(1),
(2), (4) Date: Jun. 26, 2006

(87) PCT Pub. No.: WO2005/070897
PCT Pub. Date: Aug. 4, 2005

(65) Prior Publication Data
US 2008/0221190 A1  Sep. 11, 2008

(30) Foreign Application Priority Data
Jan. 27, 2004 (HU) .................... 0400270

(51) Int. Cl.
*A61K 31/4174* (2006.01)
*C07D 233/56* (2006.01)
(52) U.S. Cl. .................... 514/399; 548/341.1
(58) Field of Classification Search ......... 514/399; 548/341.1

See application file for complete search history.

(56) References Cited

OTHER PUBLICATIONS

Rostein, et al, abstract of "The synthesis and antifungal activity of the enantiomers of butoconazole nitrate," Tetrahedron: Asymmetry. vol. 4 (Issue 7), Jul. 1993.*
"1-[4-(4-Chlorophenyl)-2- . . . " by Keith A.M. Walker et al. (Journal of Medicinal Chemistry, 1978, vol. 21, No. 8).

\* cited by examiner

*Primary Examiner*—Kamal A Saeed
*Assistant Examiner*—Janet L. Coppins
(74) *Attorney, Agent, or Firm*—Jonathan Myers; Andrew Wilford

(57) ABSTRACT

One object of the invention is high purity butoconazole nitrate of the formula (I) (I) containing maximum 0.1 wt % of chemical impurities, wherein at least 95% of the particles of the substance are below 75 μm by diameter, whereas at least 99% of the particles are below 250 μm by diameter, and process for its preparation. A pharmaceutical composition comprising as active ingredient, high purity butoconazole nitrate of specified particle size in admixture with known auxiliaries is also within the scope of the invention.

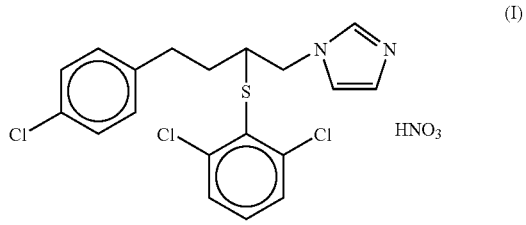

(I)

8 Claims, No Drawings

HIGH PURITY BUTOCONAZOLE NITRATE WITH SPECIFIED PARTICLE SIZE AND A PROCESS FOR THE PREPARATION THEREOF

One object of the invention is high purity butoconazole nitrate with specified particle size and a process for the preparation thereof. Another object of the invention is a pharmaceutical composition containing high purity butoconazole nitrate with specified particle size in admire with auxiliaries known per se.

Butoconazole nitrate (chemical name: 1-[4-(4-chlorophenyl)-2-(2,6-dichloro-phenylthio)-n-butyl]-imidazol nitrate) is a compound of the formula (I),

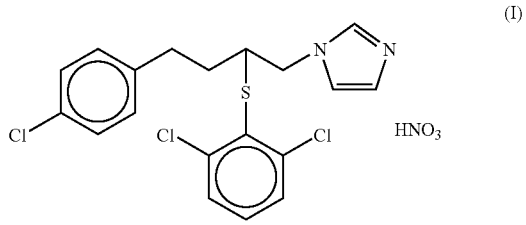

(I)

it belongs among the aryl-ethylimidazole compounds, has fungicidal activity and may be used for the treatment of vaginal infections caused primarily by *Candida albicans*. Azoles exert their antifungal effect via modifying the ergosterol synthesis of fungus cells; more particularly, imidazoles inhibit the 14α-demethylase enzyme, thereby bringing about an increased level of 14α-methyl sterols which, in turn, causes an alteration of cell membrane permeability leading to the destruction of the fungus cells (Tetrahedron: Asymmetry Vol 4, No. 7, pp. 1521-1526, 1993).

The first process for the preparation of the butoconazole nitrate is a multistep synthesis disclosed in the U.S. Pat. No. 4,078,071 patent specification. Here two reaction routes are given for the preparation of the key intermediate of the formula (IV) (1-[4-(4-chlorophenyl)-2-hydroxy-n-butyl]-imidazole).

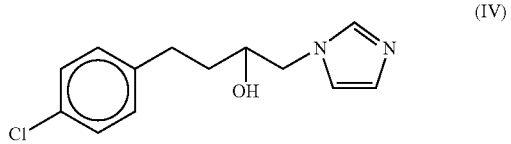

(IV)

According to one of them first an epoxy compound is prepared from an aromatic aldehyde or from an olefinic compound having a terminal double bond; then the epoxy compound is reacted with imidazole to yield the key intermediate. The aromatic aldehyde (VIII)

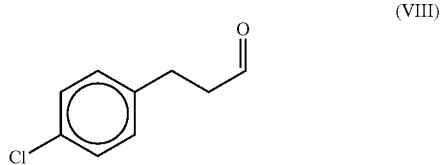

(VIII)

is treated with expensive and hazardous reagents (trimethylsulfoxonium iodide and sodium hydride) in dry dimethyl sulfoxide and the epoxide formed in the reaction is isolated after a complicated work-up. The epoxide so obtained is converted to the imidazole derivate in a time consuming reaction in the presence of dimethylformamide, then the key intermediate of the formula (IV) (1-[4-(4-chlorophenyl)-2-hydroxy-n-butyl]-imidazole) is isolated and purified in an additional step. From the compounds having terminal double bond (VII)

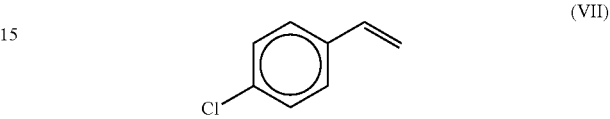

(VII)

the epoxide is obtained via a highly explosive peracidic oxidation step and the epoxide is then converted into (1-[4-(4-chlorophenyl)-2-hydroxy-n-butyl]-imidazole) (IV) in a manner described above.

In the other reaction route a poisoning aromatic α-halo-keto compound is used as starting material which is reacted with imidazole to give the corresponding keto-imidazole which, in turn, is reduced with a complex metal hydride—a reagent with potential hazards—to yield the key intermediate (IV). The reaction mixture is worked up in an involved manner.

The synthesis way described in J. Med. Chem., 1978, Vol. 21, No. 8, pp 840-843 is as follows: 1-chloro-4-chlorophenyl-2-butanol (II)

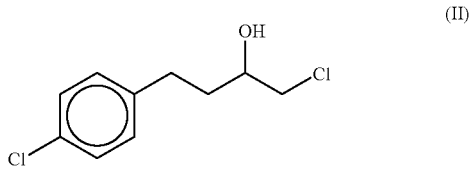

(II)

is treated with the imidazole (III)

(III)

in the presence of sodium hydride reagent in dimethylformamide solvent. This substitution reaction takes a long time and gives the (1-[4-(4-chlorophenyl)-2-hydroxy-n-butyl]-imidazole) (IV) with a poor yield (51.7%). In the next step of the butoconazole nitrate synthesis (1-[4-(chlorophenyl)-2-hydroxy-n-butyl]-imidazole) (IV) is treated with thionyl chloride (which is at once a reagent and a solvent) at 65-70° C. to yield 1-[4-(4-chlorophenyl)-2-chloro-n-butyl]-imidazole of the formula (V).

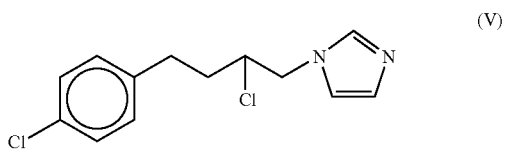 (V)

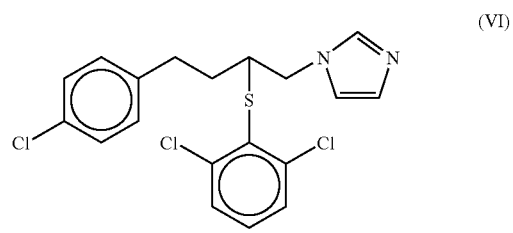 (VI)

The reaction mixture is then evaporated to dryness. The removal of the excess thionyl chloride, a highly corrosive substance, requires special equipment; the same applies to waste treatment, an operation which also involves an environmental risk. The residue is dissolved in dichloromethane, the solution is made alkaline by adding aqueous potassium carbonate solution. Phases are separated, the organic layer is washed with water, dried on magnesium sulphate and evaporated to give 1-[4-(4-chlorophenyl)-2-chloro-n-butyl]-imidazole (V), as a gum. Said gum is dissolved in acetone and reacted with 2,6-dichlorothiophenol in the presence of potassium carbonate with a long reaction time. After the reaction has been finished, the inorganic salts are removed by filtration, the solvent is evaporated, and the residue is partitioned between water and ether. Butoconazole nitrate is precipitated with nitric acid from the ethereal layer. The end-product crystals in white plates from a mixture of acetone and ethyl acetate (yield: 84%).

Our aim was to provide a process by which the active agent can be prepared in high purity via reaction steps producing good yields and besides that said steps require neither solvents that are highly flammable and explosive (ether), carcinogenic (dimethylformamide) or corrosive (thionylchloride), nor reagents (e. g. sodium hydride) that are highly flammable or explosive.

We have surprisingly found that when the starting material 1-chloro-4-chlorophenyl-2-butanol (II) is reacted with the imidazole (III) in a mixture of toluene and aqueous sodium hydroxide solution in the presence of a phase transfer catalyst, the (1-[4-(4-chlorophenyl)-2-hydroxy-n-butyl]-imidazole) (IV) key intermediate is obtained with short reaction time and excellent yield (95%).

Next we studied alternative solvents to replace the thionyl chloride in solvent function in the reaction step converting (1-[4-(4-chlorophenyl)-2-hydroxy-n-butyl]-imidazole) (IV) into (1-[4-(4-chlorophenyl)-2-chloro-n-butyl]-imidazole) (V). In the inert solvents which could be taken into account such as dichloromethane, toluene, chlorobenzene and dimethylformamide, the chlorinating reaction yielded a sticky reaction mixture which couldn't be processed. We have surprisingly found, however that when (1-[4-(4-chlorophenyl)-2-hydroxy-n-butyl]-imidazole) (IV) is dissolved in 1,2-dichloroethane and reacted with approximately equimolar amount of thionyl chloride reagent in the presence of catalytic amount of dimethylformamide at 30-35° C. temperature, a crystal suspension is obtained which is easy-to-stir during the whole reaction time, resulting in that chlorination proceeds completely giving 1-[4-(4-chlorophenyl)-2-chloro-n-butyl]-imidazole (V) in quantitative yield. Being the compound sufficiently pure, it is not isolated, but separated by extraction and reacted directly with 2,6-dichlorothiophenol in methyl isobutyl ketone to give 1-[4-(4-chlorophenyl)-2-(2,6-dichlorophenylthio)-n-butyl]-imidazole (VI) (butoconazole).

The butoconazole from the methyl isobutyl ketone solution is isolated in the form of high purity nitrate salt (maximum individual impurity 0.10%) by the addition of concentrated nitric acid.

The butoconazole nitrate active agent generally is incorporated into an ointment and marketed in such form. To obtain a composition of adequate quality at least 95% of the active agent particles should be below 75 μm by diameter and at least 99% of them should be below 250 μm.

Our aim was to develop a process which provides the product with the above specified particle size. We have surprisingly found that particles within the desired size range can be prepared without pulverization—a step requiring special machinery—in such a manner that the butoconazole nitrate is dissolved in a mixture of methanol and methyl isobutyl ketone and this hot solution is added under stirring to methyl isobutyl ketone precooled to −5° C. or below this temperature. Under such conditions an end-product of the desired particle size is obtained.

Accordingly, one object of the invention is high purity butoconazole nitrate of the formula (I) (chemical name: 1-[4-(4-chlorophenyl)-2-(2,6-dichlorophenylthio)-n-butyl]-imidazole nitrate) containing maximum 0.1 wt % chemical impurity.

Another object of the invention is a process for the preparation of the product mentioned above, said process comprising the steps a) reacting 1-chloro-4-chlorophenyl-2-butanol with the imidazole of the formula (III) to yield a compound of the formula (IV).

b) reacting the compound of the formula (IV) obtained in step a), with thionyl chloride to yield a compound of the formula (V); and c) reacting the compound of the formula (V) obtained in step b), with 2,6-dichlorothiophenol, characterized in that step a) is performed in a mixture of a water immiscible solvent and an aqueous solution of alkali metal hydroxide or carbonate in the presence of a phase transfer catalyst;

step b) is accomplished in 1,2-dichloroethane solvent in the presence of dimethylformamide, whereas 1-1.2 mol of thionyl chloride reagent is used based on the amount of the compound of the formula (IV); and step c) is carried out without isolation of the product (VI); and to the butoconazole (VI) being in solution as obtained in step c) nitric acid is added and the product is isolated as a nitrate salt.

In a preferred embodiment of the invention the water immiscible solvent is an aromatic hydrocarbon, the alkali metal hydroxide or carbonate is sodium hydroxide or sodium carbonate and in step c), 1.1 mol of thionyl chloride is used.

In another preferred embodiment of the invention the aromatic hydrocarbon is toluene.

Further, an object of the invention is high purity butoconazole nitrate containing maximum 0.1 wt % of chemical impurity, wherein at last 95% of the particles of the substance are below 75 μm by diameter, whereas at least 99% of the particiles are below 250 μm by diameter.

Still another object of the invention is a process for the preparation of the product mentioned above starting from high purity butoconazole nitrate, in such a manner that the starting material is dissolved in a mixture of methanol and methyl isobutyl ketone of 1-1.25:1 ratio (v/v), cooled to a temperature between 5° C. and −15° C. and the product obtained is isolated. In a preferred embodiment of the process the cooling temperature is between −5° C. and −10° C. and the methanol/methyl isobutyl ketone ratio is 1.25:1 (v/v).

A pharmaceutical composition containing the above defined product prepared by the above process in admixture with auxiliaries known per se is also within the scope of the invention.

The invention is further illustrated by the following non-limiting Examples.

EXAMPLE 1

Preparation of (1-[4-(4-chlorophenyl)-2-hydroxy-n-butyl]-imidazole) (IV)

To a solution of 56.7 g (0.26 mol) of 1-chloro-4-chlorophenyl-2-butanol (J. of Medicinal Chemistry, 1978. Vol. 21. No. 8. p. 842) in 200 ml of toluene 36.2 g (0.9 mol) of sodium hydroxide dissolved in 100 ml of water, 6.4 g (0.028 mol) of benzyltriethyammonium chloride and 35.2 g (0.51 mol) of imidazole (III) are added. The reaction mixture is heated at 93-95° C. for one hour then the temperature is returned to about 60° C., the phases are separated and to the organic layer water (100 ml) is added. The mixture is first stirred at 22-25° C. for 1 hour then at 0-5° C. for two hours. The crystals are separated by filtration, washed with water (2×35 ml) of 0-5° C. to yield 74 g of wet (1-[4-(4-chlorophenyl)-2-hydroxy-n-butyl]-imidazole) which is dried at maximum 50° C. in vacuo to give 61.6 g (95%) of the product. Recrystallization from ethyl acetate gives 52.4 g (85%) of dry product melting at 104-106° C.

EXAMPLE 2

Preparation of 1-[4-(4-chlorophenyl)-2-(2,6-dichlorophenylthio)-n-butyl]-imidazole nitrate (I)

25 g (0.1 mol) of 1-[4-(4-chlorophenyl)-2-hydroxy-n-butyl]-imidazole (IV) is suspended in 1,2-dichloroethane (125 ml), to this suspension dimethylformamide (1 ml) and thionyl chloride (13.6 g; 0.11 mol) are added at 30-32° C. and the reaction mixture is kept at 35-38° C. for 1.5 hour under stirring. After the chlorination has been finished the homogenous solution is cooled to 15-18° C., the excess of thionyl choride is decomposed with water (10 ml) then again water (80 ml) is added to the solution. After stirring at 20-22° C. for 0.5 hour the phases are separated and the organic layer is extracted with water (30 ml). To the aqueous solution methyl isobutyl ketone (250 ml) is added and the pH of the mixture is adjusted to 8.5-9 with 15 g (0.14 mol) of sodium carbonate dissolved in water (70 ml). The mixture is stirred at 22-25° C. for 0.5 hour, phases are separated, from the organic layer an 50 ml portion is distilled off to remove water and to the remaining solution 26.8 g (0.15 mol) of 2,6-dichloro-thiophenol and 40 g (0.29 mol) of dry potassium carbonate are added. The suspension is stirred at 105-108° C. under nitrogen for 3-4 hours. After the reaction has been finished the inorganic salts are removed by filtration at 22-25° C., the filtrate is washed and clarified with activated carbon and the pH of the clear solution is adjusted to 3-3.5 by adding about 8-9 ml of 65% nitric acid. The solution is stirred at the same temperature for 1 hour then the temperature is lowered to 8-12° C. The crystals obtained are filtered and washed to give 48 g of wet 1-[4-(4-chlorophenyl)-2-(2,6-dichlorophenylthio)-n-butyl]-imidazole nitrate corresponding to 42.6 g (90%) of dry product.

EXAMPLE 3

Preparation of 1-[4-(4-chlorophenyl)-2-2,6-dichlorophenylthio)-n-butyl]-imidazole nitrate Having Specified Particle Size 48 g of wet 1-[4-(4-chlorophenyl)-2-(2,6-dichlorophenylthio)-n-butyl]-imidazole-nitrate obtained as described in Example 2, is dissolved in a mixture of methanol (120 ml) and methyl isobutyl ketone (96 ml) at 65-70° C. and this solution is added in thin stream to 96 ml of methyl isobutyl ketone cooled to −5° C. The crystal suspension formed is kept at 0-10° C. under stirring for 1 hour, then filtered off, washed with methyl isobutyl ketone (2×15 ml) of 0-5° C. and dried at 50° C. in vacuo until its weight is constant.

Dry weight: 40.5 g (95%)

Total amount of impurities: 0.05% (determined by HPLC)

Particle size: <75 μm 97.4%; <250 μm 100%.

The results given above were obtained by the analytical methods as follow:

A. Details of the HPLC Method:

Type of the apparatus: Spectra System/TSP (manufacturer: Thermo Separation Products, USA)

Column: LiChrospher RP-18, 250×4.0 mm I.D., 5 μm (Merck, Germany, Cat. No.: 1.50983)

Mobile phase: methanol: buffer=8:2

Buffer: 2.18 g $KH_2PO_4$+4.18 g $K_2HPO_4.3H_2O$ dissolved in 1000 ml of distilled water; MeOH (HPLC Gradient grade, Merck, Germany, Cat. No.: 1.06007.2500) $KH_2PO_4$ (p.a., Merck, Germany, Cat. No.: 1.04877.1000) $K_2HPO_4$-$3H_2O$ (p.a., Merck, Germany, Cat. No.: 1.05099.1000)

Flow rate: 1.0 ml/min

Temperature: 40° C.

Detection: UV 229 nm

Solvent for sampling: eluent

Sample concentration: 1.0 mg/ml

Injected volume: 10 μl

Duration of analysis: 40 min

Evaluation: area normalization method.

Approximative retention time: 11.9 min

B. Particle Size:

Particle size was determined by sieve analysis using an Alpine sieve operated by a jet of air.

The invention claimed is:

1. A process for the preparation of a high purity butoconazole nitrate salt of the formula (I)

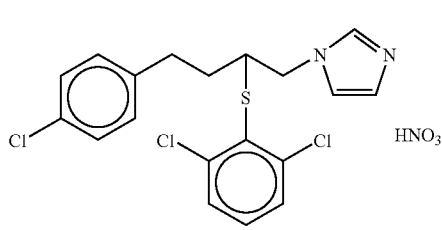

(I)

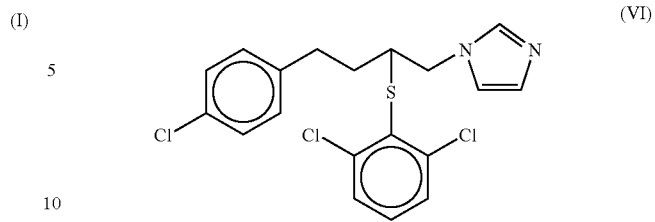

(VI)

comprising the steps of:
a) reacting 1-chloro-4-chlorophenyl-2-butanol with imidazole in a mixture of a water immiscible solvent and an aqueous solution of alkali metal hydroxide or carbonate in the presence of a phase transfer catalyst to yield a compound of the Formula IV

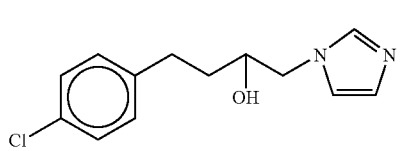

(IV)

(b) reacting the compound formula of the (IV) obtained in step a), with thionyl chloride in 1,2-dichloroethane as a solvent in the presence of dimethylformamide, whereas 1-1.2 mol of thionyl chloride reagent is used based on the amount of the compound of the formula (IV) to yield a compound of the formula (V)

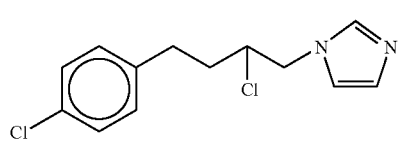

(V)

and
(c) reacting the compound of the formula (V) obtained in step b), with 2,6-dichlorothiophenol to obtain the compound of the Formula (VI)

and without isolation of the compound of the Formula (VI), which remains in solution, adding nitric acid and isolating as a product the butoconazole nitrate salt of the Formula (I) having a maximum 0.1 wt % of chemical impurities.

2. A process according to claim 1, wherein according to step (a) the water immiscible solvent is an aromatic hydrocarbon.

3. A process according to claim 2, wherein the aromatic hydrocarbon is toluene.

4. A process according to claim 1, wherein according to step (a) the alkali metal hydroxide or carbonate is respectively sodium hydroxide or sodium carbonate.

5. A process according to claim 1, wherein according to step b), thionyl chloride is used in an amount of 1.1 mol per mole of the compound of the Formula (IV).

6. A process for the preparation of a high purity butoconazole nitrate salt, wherein at least 95% of the particles of the salt are below 75 μm in diameter, and whereas at least 99% of the particles of the salt are below 250 um in diameter, which comprises the steps of:
   (a) dissolving the butoconazole nitrate salt starting material in a mixture of methanol and methyl isobutyl ketone of 1-1.5:1 ratio (v/v) to form a solution;
   (b) adding the solution formed according to step (a) to methyl isobutyl ketone cooled to a temperature between 5° and −15° C.' and
   (c) isolating the desired product.

7. A process according to claim 6, wherein according to step (b) the cooling temperature is between −5° C. and −10° C.

8. A process according the claim 6, wherein according to step (a) the mixture of methyl alcohol and methyl isobutyl ketone for dissolving the butoconazole nitrate salt starting material is employed in a volume ratio of methanol/methyl isobutyl ketone of 1.25:1.

* * * * *